United States Patent
Mestl et al.

(10) Patent No.: US 9,873,114 B2
(45) Date of Patent: Jan. 23, 2018

(54) POST-GILDING OF PD-AU-COATED SHELL CATALYSTS

(71) Applicants: Gerhard Mestl, Munich (DE); Peter Scheck, Gilching (DE); Alfred Hagemeyer, Sunnyvale, CA (US); Carolin Fischer, Rosenheim (DE); Roman Bobka, Munich (DE)

(72) Inventors: Gerhard Mestl, Munich (DE); Peter Scheck, Gilching (DE); Alfred Hagemeyer, Sunnyvale, CA (US); Carolin Fischer, Rosenheim (DE); Roman Bobka, Munich (DE)

(73) Assignee: CLARIANT PRODUKTE (DEUTSCHLAND) GMBH, Frankfurt am Main (DE)

( * ) Notice: Subject to any disclaimer, the term of this patent is extended or adjusted under 35 U.S.C. 154(b) by 0 days.

(21) Appl. No.: 14/379,262

(22) PCT Filed: Feb. 19, 2013

(86) PCT No.: PCT/EP2013/053230
§ 371 (c)(1),
(2) Date: Aug. 15, 2014

(87) PCT Pub. No.: WO2013/124252
PCT Pub. Date: Aug. 29, 2013

(65) Prior Publication Data
US 2015/0031911 A1    Jan. 29, 2015

(30) Foreign Application Priority Data
Feb. 20, 2012 (DE) .................. 10 2012 003 232

(51) Int. Cl.
*B01J 31/28* (2006.01)
*B01J 37/18* (2006.01)
(Continued)

(52) U.S. Cl.
CPC .............. *B01J 31/28* (2013.01); *B01J 23/52* (2013.01); *B01J 23/58* (2013.01); *B01J 31/38* (2013.01);
(Continued)

(58) Field of Classification Search
CPC . B01J 23/44; B01J 23/52; B01J 35/008; B01J 37/00; B01J 37/04; B01J 37/0223; B01J 37/18
(Continued)

(56) References Cited

U.S. PATENT DOCUMENTS

| 6,015,769 A | 1/2000 | Wang |
| 6,096,844 A | 8/2000 | Fushimi et al. |

(Continued)

FOREIGN PATENT DOCUMENTS

| DE | 198 27 844 | 12/1999 |
| DE | 695 20 332 | 8/2001 |

(Continued)

OTHER PUBLICATIONS

PCT International Search Report for PCT/EP2013/053230, dated Jul. 24, 2013.
(Continued)

*Primary Examiner* — Patricia L. Hailey
(74) *Attorney, Agent, or Firm* — Anthony A. Bisulca

(57) ABSTRACT

The invention relates to a method for producing a shell catalyst that is suitable for producing vinyl acetate monomer (VAM). The invention further relates to a shell catalyst that is obtainable by the method according to the invention and to the use of the shell catalyst according to the invention for producing VAM.

14 Claims, 1 Drawing Sheet

(51) Int. Cl.
  *B01J 37/02* (2006.01)
  *B01J 23/52* (2006.01)
  *B01J 23/58* (2006.01)
  *B01J 35/00* (2006.01)
  *C07C 67/055* (2006.01)
  *B01J 31/38* (2006.01)
  *C07C 67/05* (2006.01)

(52) U.S. Cl.
  CPC ......... *B01J 35/008* (2013.01); *B01J 37/0205* (2013.01); *B01J 37/18* (2013.01); *C07C 67/05* (2013.01); *C07C 67/055* (2013.01); *B01J 2231/49* (2013.01)

(58) Field of Classification Search
  USPC .......................................... 502/330, 339, 344
  See application file for complete search history.

(56) References Cited

U.S. PATENT DOCUMENTS

| | | | |
|---|---|---|---|
| 8,466,082 B2 | 6/2013 | Hagemeyer et al. | |
| 8,927,452 B2 | 1/2015 | Hagemeyer et al. | |
| 9,334,226 B2 | 5/2016 | Bobka et al. | |
| 2001/0048970 A1 | 12/2001 | Hagemeyer et al. | |
| 2004/0259723 A1 | 12/2004 | Wagner et al. | |
| 2005/0181940 A1* | 8/2005 | Wang | B01J 23/464 502/330 |
| 2006/0135809 A1* | 6/2006 | Kimmich | B01J 23/44 560/241 |
| 2010/0185010 A1 | 7/2010 | Hagemeyer et al. | |
| 2010/0190638 A1* | 7/2010 | Hagemeyer | B01J 23/42 502/161 |
| 2010/0197488 A1* | 8/2010 | Hagemeyer | B01J 2/16 502/242 |
| 2010/0197956 A1* | 8/2010 | Hagemeyer | B01J 21/16 560/208 |
| 2010/0261603 A1* | 10/2010 | Hagemeyer | B01J 23/44 502/339 |
| 2010/0273644 A1* | 10/2010 | Hagemeyer | B01J 23/56 502/243 |
| 2011/0166010 A1* | 7/2011 | Hagemeyer | B01J 21/06 502/74 |
| 2011/0319655 A1 | 12/2011 | Hagemeyer et al. | |
| 2012/0289737 A1* | 11/2012 | Hagemeyer | B01J 37/08 560/243 |
| 2013/0172603 A1* | 7/2013 | Hagemeyer | B01J 21/066 560/261 |
| 2015/0011386 A1 | 1/2015 | Hagemeyer et al. | |
| 2015/0126360 A1* | 5/2015 | Mestl | B01J 37/16 502/330 |
| 2015/0126361 A1 | 5/2015 | Mestl et al. | |

FOREIGN PATENT DOCUMENTS

| | | | |
|---|---|---|---|
| DE | 10 2007 025 317 | 12/2008 | |
| DE | 10 2007 025 442 | 12/2008 | |
| DE | 10 2007 025 356 | 1/2009 | |
| DE | 10 2008 032 080 | 1/2010 | |
| DE | 10 2010 026 462 | 1/2012 | |
| WO | WO 99/62632 | 12/1999 | |
| WO | 2013/124252 | * 8/2013 | .............. B01J 37/18 |

OTHER PUBLICATIONS

International Preliminary Report on Patentability for PCT/EP2013/053230, dated Aug. 26, 2014.
English Abstract for DE 10 2008 032 080, Jan. 14, 2010.
English Abstract for DE 10 2007 025 317, Dec. 4, 2008.

* cited by examiner

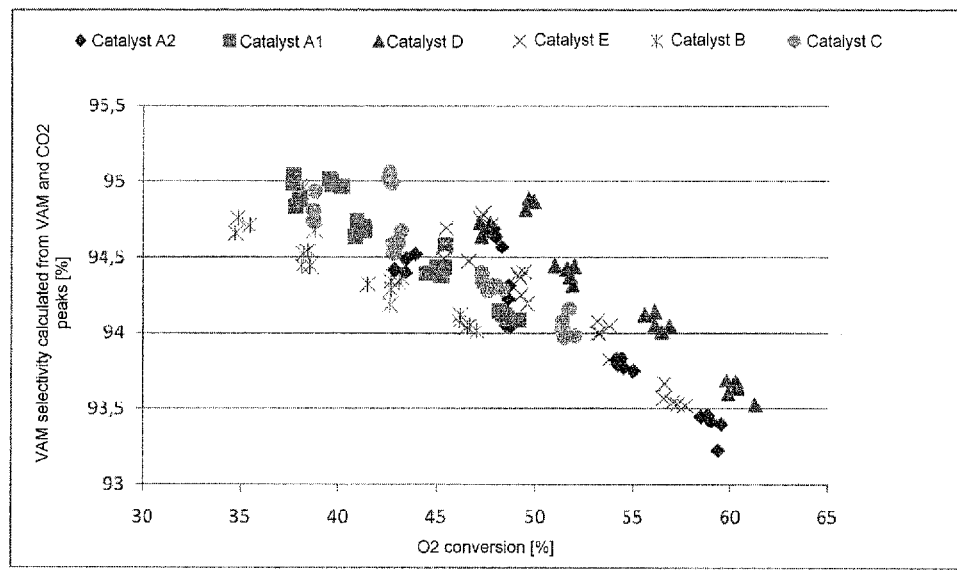

POST-GILDING OF PD-AU-COATED SHELL CATALYSTS

The present invention relates to a novel process for producing an eggshell catalyst suitable for preparation of vinyl acetate monomer (VAM). The present invention additionally relates to an eggshell catalyst obtainable by the process according to the invention, and to the use of the inventive eggshell catalyst for preparation of VAM.

Supported catalysts containing palladium and gold have already been known for some time. VAM is typically prepared in the presence of catalysts containing palladium and gold from a reaction mixture composed of ethylene, oxygen and acetic acid. Various production processes for such supported catalysts are already known. For example, precursor compounds containing the corresponding metals are applied in dissolved form, preferably in an aqueous solution, to the surface of a support body. The support body containing the corresponding precursor compounds is then typically calcined under oxidizing conditions in a high-temperature oven, converting the metal-containing precursor compounds to the metal oxides. Subsequently, the support bodies containing the corresponding metal oxides are then subjected to the reduction to elemental metals.

Vinyl acetate monomer is an important synthesis unit for the preparation of polyvinyl acetate, of vinyl acetate copolymers (such as ethylene-vinyl acetates or ethylene-vinyl alcohol copolymers) and of polyvinyl alcohol. Because of the broad field of use of these polymers, for example as a binder in the construction, paints and coatings sector, and as a raw material for the adhesives, paper and textile industries, there continues to be a high demand for VAM and for constant improvement in the activity and selectivity of catalysts for preparation thereof.

Normally, in the synthesis of VAM, eggshell catalysts are used, where elemental Pd and Au are present in an outer shell of a catalyst support body. For the preparation thereof, a mixed solution of a Pd-containing precursor compound and an Au-containing precursor compound is generally applied to a catalyst support body, the latter is subsequently dried, and the metal components in the precursor compounds are converted to elemental metals. The Pd/Au combination generally leads to good selectivity and activity of the catalyst. Because of the high capital intensity of corresponding VAM production plants and the increasingly high raw material costs, especially for ethylene, however, there is a constant need to optimize the economic viability of the process for preparing VAM by means of improved catalysts.

It was therefore an object of the present invention to provide a process for producing an eggshell catalyst, which leads to eggshell catalysts superior to existing catalysts in terms of activity and selectivity in the synthesis of VAM.

This object was achieved by a process according to the invention with which eggshell catalysts can be produced with significantly increased selectivity and activity for VAM.

The process according to the invention for producing an eggshell catalyst is characterized by the following process steps:

(a) subjecting a bed of a catalyst support body (support body) to a circulating motion;
(b) contacting an atomized aqueous solution comprising a Pd-containing precursor compound and an Au-containing precursor compound with the bed of the support body subjected to the circulating motion by spraying, or contacting an atomized aqueous solution comprising a Pd-containing precursor compound and an atomized aqueous solution comprising an Au-containing precursor compound with the bed of the support body subjected to the circulating motion by spraying;
(c) contacting an atomized aqueous solution comprising an Au-containing precursor compound with the support body obtained after step (b); and
(d) metal reduction by subjecting the support body obtained in step (c) to a thermal treatment in a non-oxidizing atmosphere.

In step (c) of the process according to the invention, it is likewise preferable that the contacting takes place by spraying the solution onto a bed of the catalyst support body subjected to a circulating motion.

BRIEF DESCRIPTION OF THE DRAWING

FIG. 1 is a reproduction of the values from tables 1 and 2.

In one embodiment of the process according to the invention, in step (c), aside from the catalytic Au precursor compound, no further precursor compound of catalytically active metals, more particularly no Pd precursor compounds, is applied.

The term "eggshell catalyst" is understood to mean a catalyst comprising a support body and a shell comprising catalytically active material, where the shell may be formed in two different ways:

Firstly, a catalytically active material may be present in the outer region of the support body, such that the material of the support body serves as a matrix for the catalytically active material, and the region of the support body impregnated with the catalytically active material forms a shell around the non-impregnated core of the support body. Secondly, an additional layer with a catalytically active material present therein may be applied to the surface of the support body. This layer thus forms an additional material coat formed as a shell around the support body. In the latter variant, the support body material is not a constituent of the shell; instead, the shell is formed by the catalytically active material itself or a matrix material comprising a catalytically active material. In one embodiment of the present invention, preference is given to the former variant of an eggshell catalyst.

In the catalyst produced by the process according to the invention, the metals are either in monoatomic form or in the form of aggregates. However, they are preferably in the form of aggregates. These monoatomic atoms or aggregates are dispersed predominantly homogeneously within the shell of the eggshell catalyst. An aggregate is understood to mean the clustering of several metal atoms to form a composite which is between monoatomic form and metallic structure. This also includes what are called metal clusters.

The shell thickness of the outer shell of the support body is preferably 1 to 70%, more preferably 2 to 60%, even more preferably 3 to 50% and most preferably 4 to 40% of half the total thickness of the support body. Said percentage is based on half the total thickness because, according to the shape of the support body in the production, for example through spray impregnation with a precursor compound-containing solution, the precursor compound penetrates either from two outer surfaces into the support body material (sphere), or, when the support body material has a more complex shape, for example that of a hollow cylinder, there is an outer surface and an inner surface into which the precursor compound penetrates. In the case of support body materials differing from spherical geometry, the total thickness of the support is measured along the longest support body axis.

The outer shell boundary is equated to the outer limit of the metal-containing support body. The inner shell boundary is understood to mean the boundary of the outer metal-containing shell within the support body which is removed from the outer shell boundary to such an extent that 95% by weight of the total amount of metal present in the support body is within the outer shell. At the same time, the shell thickness, however, is preferably not greater than 70%, more preferably not greater than 60%, even more preferably not greater than 50%, even more preferably still not greater than 40% and most preferably not greater than 30%, based in each case on half the total thickness of the support body.

Preferably, the metal-impregnated support body contains not more than 5% of the total amount of metal in the inner region thereof, i.e. within the region bounded on the outside by the inner shell boundary of the metal shell.

With regard to the shell thickness of the catalyst, the maximum metal concentration is preferably in the region of the outer shell, more preferably at the outer edge of the outer shell, i.e. close to the geometric catalyst surface. The metal concentration preferably decreases in the direction of the inner shell boundary.

The support body is preferably composed of an inert material. It may be porous or nonporous. However, the support body is preferably porous. The support body preferably consists of particles having a regular or irregular shape, for example spheres, tablets, cylinders, solid cylinders or hollow cylinders, rings, stars or other shapes, and has a range of 1 to 10 mm, preferably 3 to 9 mm, in its dimensions, for example diameter, length or width. Spherical, i.e., for example, ball-shaped, particles having a diameter of 3 to 8 mm are preferred in accordance with the invention. The support body material may be composed of any nonporous and porous substance, preferably porous substance. Examples of materials for this purpose are titanium oxide, silicon oxide, aluminum oxide, zirconium oxide, magnesium oxide, silicon carbide, magnesium silicate, zinc oxide, zeolites, sheet silicates and nanomaterials, for example carbon nanotubes or carbon nanofibers, preferably when the support body material itself is a heterogeneous catalyst. The aforementioned oxidic support body materials can be used, for example, in the form of mixed oxides or defined compositions, for example $TiO_2$, $SiO_2$, $Al_2O_3$, $ZrO_2$, MgO, SiC or ZnO. In addition, it is possible with preference to use carbon blacks, ethylene black, charcoal, graphite, hydrotalcites or further support body materials known per se to those skilled in the art in various possible polymorphs. The support body materials can preferably be doped, for instance, with alkali metals or alkaline earth metals, or else with phosphorus, halide and/or sulfate salts. The oxidic support body materials may also have a proportion of zirconium dioxide. The proportion of $ZrO_2$ in these materials here is preferably in the range from 5 to 20% by weight, based on the total weight of the support body material.

The BET surface area of the support body material without the coating with the precursor compounds is 1 to 1000 $m^2$/g, preferably 10 to 600 $m^2$/g, more preferably 20 to 400 $m^2$/g and most preferably between 80 and 170 $m^2$/g. The BET surface area is determined by the 1-point method by absorption of nitrogen to DIN 66 132.

In addition, it may be preferable that the integral pore volume of the support body material (determined to DIN 66133 (Hg porosimetry)) without the coating with the precursor compound is greater than 0.1 mL/g, preferably greater than 0.18 mL/g.

The support body is typically produced by subjecting a multitude of support bodies to a "batch" process, wherein individual process steps subject the shaped bodies to comparatively high mechanical stresses, for example through use of stirring and mixing tools. In addition, the eggshell catalyst produced by the process according to the invention can be severely mechanically stressed in the course of filling of a reactor, which can result in unwanted evolution of dust and damage to the support body, especially to the catalytically active shell thereof, which is in an outer region.

Especially in order to keep the abrasion of the catalyst produced by the process according to the invention within acceptable limits, the eggshell catalyst has a hardness of greater than/equal to 20 N, preferably of greater than/equal to 25 N, further preferably of greater than/equal to 35 N and most preferably of greater than/equal to 40 N. The hardness is ascertained by means of an 8 M tablet hardness tester from Dr. Schleuniger Pharmathron AG on 99 eggshell catalysts as an average, after drying the catalyst at 130° C. for two hours, with the instrument settings as follows:

Distance from the shaped body: 5.00 mm
Time delay: 0.80 s
Advance type: 6 D
Speed: 0.60 mm per second The hardness of the catalyst produced by the process according to the invention can be influenced, for example, by means of deviations in certain parameters in the process for producing the support body, for example through the calcination time and/or the calcination temperature of the support body. The calcination just mentioned is not a calcination of the support body impregnated with the metal-containing precursor compounds, but merely a calcining step for production of the support body before the precursor compounds are applied.

It is additionally preferable that 80% of the integral pore volume of the support body is formed by mesopores and macropores, preferably at least 85% and most preferably at least 90%. This counters any reduction in activity of the catalyst produced by the process according to the invention that is caused by diffusion limitation, especially in the case of metal-containing shells with comparatively high thicknesses. In this regard, the terms "micropores", "mesopores" and "macropores" shall be understood to mean pores having, respectively, a diameter of less than 2 nm, a diameter of 2 to 50 nm and a diameter of greater than 50 nm.

The activity of the eggshell catalysts produced by the process according the invention generally depends on the amount of metal loading in the shell: in general, the more metal is present in the shell, the higher it is. The thickness of the shell has a relatively minor influence on the activity here, but is a crucial parameter in terms of selectivity of the catalysts. In general, for the same metal loading of the catalyst support, the lower the thickness of the outer shell of the catalyst, the higher the selectivity of the eggshell catalysts produced by the process according to the invention. It is thus crucial to set an optimal ratio of metal loading to shell thickness in order to ensure a maximum selectivity combined with maximum activity. In accordance with a further preferred embodiment of the catalyst produced by the process according to the invention, therefore, the shell of the catalyst has a thickness in the range from 5 μm to 2000 μm, preferably from 10 μm to 5000 μm, more preferably from 15 to 1000 μm. If the eggshell catalyst is to be used, for example, as a catalyst for vinyl acetate synthesis, the shell thickness thereof is preferably in the range from 10 μm to 400 μm, more preferably in the range from 50 μm to 300 μm.

The thickness of the shell can be measured optically by means of a microscope. Specifically, the region in which the metal is deposited appears black, while the noble metal-free regions appear white. The boundary between noble metal-containing and -free regions is generally very sharp and clearly visually apparent. Should the aforementioned boundary not be sharp and accordingly not be clearly visually apparent, the thickness of the shell—as mentioned above— corresponds to the thickness of a shell measured proceeding from the outer surface of the catalyst support in which 95% of the noble metal deposited on the support is present. In order to ensure substantially homogeneous activity of the catalyst produced by the process according to the invention over the thickness of the noble metal-containing shell, the noble metal concentration should vary only to a comparatively small degree over the shell thickness. It is therefore preferable when the profile of the noble metal concentration of the catalyst over a region of 90% of the conduct. In step (b), the precursor compounds can be sprayed on either from a mixed solution comprising the Au-containing precursor compound and the Pd-containing precursor compound, or from two solutions each containing one of the two precursor compounds. More preferably, the precursor compounds are from a single solution simultaneously onto the support body shell thickness over, with the region from the outer and inner shell boundary spaced apart by 5% of the shell thickness in each case, differs from the mean noble metal concentration of this region by a maximum of +/−20%, preferably by a maximum of +/−15% and preferably by a maximum of +/−10%. Profiles of this kind are obtainable by means of the contacting, described below, of an atomized aqueous solution comprising the precursor compound(s) onto a bed of a support body subject to circulating motion by spray application. In order to achieve the circulating motion of the bed of the support bodies, an especially suitable method is to initially charge the bed of the support bodies in a fluidized bed, a moving bed or an Innojet Aircoater as described below. The distribution just mentioned in the metal loading preferably describes a rectangular function. As well as the rectangular function, the metal loading within the shell may also describe a triangular or trapezoidal function, in which the metal concentration gradually drops from the outside inward in the shell. It is therefore preferable in accordance with the invention that any applying of precursor compounds mentioned in this application is conducted in the abovementioned manner.

The spray application of the precursor compounds in steps (b) and (c) of the process according to the invention to the support body can be sprayed on by processes known per se. However, the precursor compounds can also be sprayed onto the support body simultaneously or sequentially from two different solutions.

In the prior art, a solution comprising the precursor compounds is often applied by impregnation, by dipping the support body into the precursor compound solutions, or by the incipient wetness method. With the aid of these impregnation processes, however, it is difficult to produce an eggshell catalyst with a defined shell and a homogeneous metal distribution.

The spray application of the precursor compounds in steps (b) and (c) in the process according to the invention is preferably conducted by spraying the support body with an aqueous solution comprising the precursor compound, the solution being atomized. At the same time, a bed of the support body is subjected to a circulating motion, such that the support body can be sprayed homogeneously from all sides. The circulating motion can in principle be effected by means of any known mechanical stirring unit, for example a coating drum. However, it is preferable in accordance with the invention that the circulating motion of the support bodies is conducted by means of a process gas, for example in a moving bed, a fluidized bed or in a coating chamber of an Innojet Aircoater. In this case, the support bodies are moved by injected process gas. The process gas is preferably conducted here such that the support bodies are kept within a controlled gliding layer of the process gas. The process gas is preferably heated at the same time, such that the solvent is vaporized rapidly. In this way, the precursor compounds are present in the defined shell mentioned in the support body. The spray rate is preferably selected during the spray application such that an equilibrium is achieved between the evaporation rate of the solvent and the feed rate of the precursor compounds to the support body. This enables setting of the desired shell thickness and palladium/gold distribution in the shell. According to the spray rate, it is thus possible to infinitely adjust and optimize the shell thickness, for example up to a thickness of 2 mm. However, very thin shells having a thickness of less than 1000 µm are also possible in this way.

It is particularly preferable that the spray rate in the spray application of the precursor compounds is constant and is within the range of a mass flow of the solution comprising the precursor compound(s) from 0.1 to 15 g/min per 100 g of support bodies to be coated, more preferably 0.2 to 10 g/min per 100 g of support bodies to be coated and most preferably 0.5 to 7.5 g/min per 100 g of support bodies to be coated. In other words, the ratio of the weight of the solution sprayed on to the weight of the bed of the support body is preferably within the range from 0.001 to 0.15, more preferably 0.002 to 1 and most preferably 0.005 to 0.075. A mass flow rate or ratio above the range specified leads to catalysts having lower selectivity; a mass flow rate or ratio below the range specified does not have any adverse effects on the catalyst performance, but the time taken to produce the catalyst is very high and the production is therefore inefficient.

If a fluidized bed system is used, it is preferable when the support bodies circulate elliptically or toroidally in the fluidized bed. In order to give an idea of how the shaped bodies move in such fluidized beds, in the case of "elliptical circulation", the support bodies move in the fluidized bed in a vertical plane on an elliptical path with varying size of the main axis and secondary axis. In the case of "toroidal" circulation, the support bodies move in the fluidized bed in a vertical plane on an elliptical path with varying size of the main axis and secondary axis and in a horizontal plane on a circular path with varying radius size. On average, the support bodies in the case of "elliptical circulation" move in a vertical plane on an elliptical path, and in the case of "toroidal circulation" on a toroidal path, meaning that a support body travels helically over the surface of a torus having a vertically elliptical section.

The spraying of the precursor compounds onto the catalyst support body (support body) in steps (b) and (c) of the process according to the invention is more preferably conducted by means of a fluidized bed in a fluidized bed system. In this case, it is especially preferable that what is called a controlled gliding layer of process gas exists in the system. Firstly, the support bodies are mixed by the controlled gliding layer of process gas, in the course of which they rotate simultaneously about their own axis and are dried homogeneously by the process gas. Secondly, the support bodies, because of the consistent orbital motion of the support bodies brought about by the controlled gliding layer of process gas, pass through the spraying operation (application of the precursor compounds) with virtually constant frequency. This achieves a virtually homogeneous shell thickness, i.e. penetration depth of the noble metals into the support bodies, of a treated phase of support bodies. In addition, this achieves only comparatively small variation in the noble metal concentration over a comparatively wide range of shell thickness, meaning that the noble metal concentration describes an approximately rectangular function over a wide range of shell thickness, resulting in a substantially homogeneous activity of the resulting catalyst over the thickness of the noble metal shell. In this way, however, it is also possible to adjust the noble metal concentration in the shell such that it describes a triangular or trapezoidal function.

Suitable conventional coating drums, fluidized bed systems and moving bed systems for performance of the spray application of the precursor compounds in the process according to the invention are known in the prior art and are sold, for example, by companies such as Heinrich Brucks GmbH (Alfeld, Germany), ERWEKA GmbH (Heusenstamm, Germany), Stechel (Germany), DRIAM Anlagenbau GmbH (Erichskirch, Germany), Glatt GmbH (Binzen, Germany), D.S. Divisione Verniciatura (Osteria, Italy), HOFER-Pharma Maschinen GmbH (Weil am Rhein, Germany), L.B. Bohle Maschinen and Verfahren GmbH (Enningerloh, Germany), Lodige Maschinenbau GmbH (Paderborn, Germany), Manesty (Merseyside, Great Britain), Vector Corporation (Marion (IA), USA), Aeromatic-Fielder AG (Bubendorf, Switzerland), GEA Process Engineering (Hampshire, Great Britain), Fluid Air Inc. (Aurora, Ill., USA), Heinen Systems GmbH (Varel, Germany), Hüttlin GmbH (Steinen, Germany), Umang Pharmatech Pvt. Ltd. (Maharashtra, India) and Innojet Technologies (Lörrach, Germany). Particularly preferred fluidized bed apparatuses are sold with the Innojet® Aircoater or Innojet® Ventilus name by Innojet Technologies. Particular preference is given here to the use of the IAC-5 coater, the IAC-150 coater or the IAC-025 coater, each from Innojet.

In addition, the support body used in the process according to the invention is heated during the spray application of the solutions comprising the precursor compounds in steps (b) and (c), for example by means of heated process gas. The process gas here preferably has a temperature of 10 to 110° C., more preferably 40 to 100° C. and most preferably 50 to 90° C. Said upper limits should be observed in order to ensure that said outer shell has a small layer thickness with a high concentration of noble metal.

The process gas used is preferably air, but it is also possible to use inert gases, for example nitrogen, $CO_2$, helium, neon, argon or mixtures thereof.

As already mentioned above, the spray application of the precursor compounds onto the catalyst support bodies in steps (b) and (c) is preferably conducted by application from aqueous solutions. Suitable solvents for the transition metal precursor compounds are water and mixtures of water and solvents, but preferably deionized water, in which the selected metal compound(s) is/are soluble and which, after application to the catalyst support, can be removed again easily therefrom by means of drying. Preferred solvents are unsubstituted carboxylic acids, especially acetic acid, and ketones such as acetone.

The spray application of the solutions comprising the precursor compounds is preferably accomplished in all the process steps of the process according to the invention by atomizing the solution with the aid of a spray nozzle. This is preferably done using an annular gap nozzle, which sprays a spray cloud having a plane of symmetry that runs parallel to the plane of the system base. By virtue of the 360° circumference of the spray cloud, the support bodies that fall downward in the middle are sprayed particularly homogeneously with the solution. At the same time, the annular gap nozzle, i.e. the mouth thereof, is preferably embedded completely in the apparatus which conducts the circulating motion of the support bodies.

In accordance with a further preferred embodiment of the process according to the invention, the annular gap nozzle is arranged centrally in the base of the apparatus that undertakes the circulating motion of the support bodies, and the opening of the annular gap nozzle is completely embedded in the apparatus. This ensures that the free path length of the droplets of the spray cloud before they hit a shaped body is comparatively short and, correspondingly, the droplets have comparatively little time to coalesce to larger droplets, which could counter the formation of a substantially homogeneous shell thickness.

In the process according to the invention, the solutions are preferably atomized in such a way that the solutions hit the support bodies in the form of an aerosol. The droplet size here on impact with the support bodies is preferably in the range from 1 to 100 μm, more preferably in the range from 10 to 40 μm. It has been found that an excessively small droplet size leads to catalysts having a poor activity, whereas an excessively large droplet size leads to catalysts having a poor VAM selectivity.

If the Pd-containing precursor compound and the Au-containing precursor compound are applied in step (b) from a solution, the solution preferably contains such a proportion of Pd-containing precursor compound that Pd is in the range from 0.5 to 5% by weight, more preferably within the range from 0.7 to 2.5% by weight, and such a proportion of Au-containing precursor compound that the Au content is in the range from 0.01 to 10% by weight, more preferably in the range from 0.1 to 5% by weight and most preferably in the range from 0.3 to 1% by weight, based on the atomic proportion by weight of the metal in solution.

If the Pd-containing precursor compound and the Au-containing precursor compound are applied separately from different solutions, either simultaneously or sequentially, the Pd-containing solution preferably contains Pd within the range from 0.5 to 5% by weight, and the Au-containing solution preferably contains Au within the range from 0.1 to 10% by weight, based on the atomic proportion by weight of the metal in solution.

If the metal contents are above the specified ranges in the above-specified solutions, the result is eggshell catalysts having a lower selectivity. Metal contents below the range specified have an adverse effect on the activity of the catalysts obtained.

It is possible that the spray application of the precursor compounds to the support body in step (b) is followed by a drying step, before the Au-containing support body is sprayed on in step (c). The drying step is preferably conducted below the decomposition temperature of the precursor compounds, especially at the temperatures specified above. A decomposition temperature is understood to mean the temperature at which the precursor compounds begin to decompose. The drying is effected preferably by means of the process air in the moving bed or fluidized bed, by leaving to stand under air, or in a drying oven, preferably at a temperature in the range from 60° C. to 120° C. However, it is also particularly preferable that steps (b) and (c) are directly successive, such that no drying step is conducted between them. This is effected by, immediately after the spray application of the solution(s) comprising the precursor compounds in step (b), spraying on the solution comprising the Au-containing precursor compound from step (c).

As already mentioned above, it is particularly preferable when the solution to be applied in step (b) is a mixed solution composed of a Pd-containing precursor compound and an Au-containing precursor compound. However, this does not rule out conducting step (b) by first spraying on a solution comprising a Pd- or Au-containing precursor compound by one of the abovementioned methods, then optionally drying and subsequently spraying on a solution comprising an Au- or Pd-containing precursor compound. Each of these steps may then be followed by a drying operation on the coated support body. In addition, between the spray applications of the two solutions, a step of intermediate calcination for oxidation of the precursor compound to the metal oxides can optionally be conducted. It is likewise optionally possible to conduct a step of intermediate reduction to reduce the precursor compounds to the metals. However, it is particularly preferable that neither a drying step nor a calcination step nor a reduction step is effected between the steps for spray application of the two precursor compounds in step (b).

The catalyst support body preferably contains, after step (b), a Pd content in the range from 0.5 to 2.5% by weight, more preferably in the range from 0.7 to 1.8% by weight, even more preferably in the range from 0.9 to 1.6% by weight, even more preferably in the range from 1.1 to 1.4 and, based on the total weight of the catalyst support body after the drying operation (i.e. based on the anhydrous catalyst precursor).

The catalyst support body preferably contains, after step (b), an Au content in the range from 0.1 to 1.0% by weight, more preferably in the range from 0.2 to 0.9% by weight and most preferably in the range from 0.3 to 0.7% by weight, based on the total weight of the catalyst support body after the drying operation.

The Pd-containing precursor compound and Au-containing precursor compound in steps (b) and (c) is preferably a water-soluble compound.

The Pd-containing precursor compound is preferably selected from: nitrate compounds, nitrite compounds, acetate compounds, tetraammine compounds, diammine compounds, hydrogencarbonate compounds and hydroxidic metalate compounds.

Examples of preferred Pd-containing precursor compounds are water-soluble Pd salts. In a particularly preferred embodiment of the process according to the invention, the Pd precursor compound is selected from the group consisting of $Pd(NH_3)_4(HCO_3)_2$, $Pd(NH_3)_4(HPO_4)$, ammonium Pd oxalate, Pd oxalate, $K_2Pd(oxalate)_2$, Pd(II) trifluoroacetate, $Pd(NH_3)_4(OH)_2$, $Pd(NO_3)_2$, $H_2Pd(OAC)_2(OH)_2$, $Pd(NH_3)_2$, $(NO_2)_2$, $Pd(NH_3)_4(NO_3)_2$, $H_2Pd(NO_2)_4$, $Na_2Pd(NO_2)_4$, $Pd(OAc)_2$ and freshly precipitated $Pd(OH)_2$. The preparation of freshly precipitated $Pd(OH)_2$ is preferably conducted as follows: here, preferably, a 0.1 to 40% by weight aqueous solution of tetrachloropalladate is prepared. Then a base, preferably an aqueous solution of potassium hydroxide, is added to this solution, until a brown solid, namely the $Pd(OH)_2$, precipitates out. To prepare a solution for application to the catalyst support, the freshly precipitated $Pd(OH)_2$ is isolated, washed and dissolved in an aqueous alkaline solution. The dissolution is preferably effected at a temperature in the range from 4 to 40° C., more preferably 15 to 25° C. A lower temperature is not possible because of the freezing point of water; a higher temperature brings the disadvantage that $Pd(OH)_2$ precipitates again after a certain time in the aqueous solution and does not go into solution.

In addition, it is also possible to use the Pd nitrite precursor compounds in the process according to the invention. Preferred Pd nitrite precursor compounds are, for example, those which are obtained by means of dissolution of $Pd(OAc)_2$ in an $NaNO_2$ or $KNO_2$ solution.

The Au-containing precursor compounds in steps (b) and (c) are each independently preferably selected from: acetate compounds, nitrite or nitrate compounds and hydroxidic metalate compounds.

Examples of preferred Au-containing precursor compounds are water-soluble Au salts. In a particularly preferred embodiment of the process according to the invention, the Au precursor compound is selected from the group consisting of $KAuO_2$, $NaAuO_2$, $LiAuO_2$, $RbAuO_2$, $Ba(AuO_2)_2$, $NaAu(OAc)_3(OH)$, $KAu(NO_2)_4$, $KAu(OAc)_3(OH)$, $LiAu(OAc)_3(OH)$, $RbAu(OAc)_3(OH)$, $HAu(NO_3)_4$ and $Au(OAc)_3$. It may be advisable here to make up $Au(OAc)_3$ or the $KAuO_2$ freshly in each case, by means of precipitation of the oxide, hydroxide from an auric acid solution, washing and isolating the precipitate, and taking it up in acetic acid or KOH. The Au-containing precursor compound used is more preferably potassium aurate, which is used in dissolved form for application to the support body. The preparation of a potassium aurate solution is known in the literature and can be prepared by the preparation processes disclosed in publications WO 99/62632 and U.S. Pat. No. 6,015,769. Especially preferably, the Au-containing precursor compounds in steps (b) and (c) are the same, especially $KAuO_2$.

The precursor compounds mentioned are cited merely by way of example, and it is possible to use any further precursor compounds. It is particularly preferable that the precursor compounds are essentially chloride-free. "Essentially chloride-free" is understood to mean that the empirical formula of the compound does not include any chloride, but it is not ruled out that the compound, for example as a result of the preparation, contains unavoidable contaminations of chloride. In this case, it is particularly preferable that the maximum chloride content in a solution containing the Au precursor compound does not exceed 5000 ppm, more preferably 3000 ppm and most preferably 1500 ppm, and in a solution containing the Pd precursor compound does not exceed 600 ppm, more preferably 300 ppm and most preferably 100 ppm.

It is particularly preferable that, in step (b), a Pd-containing precursor compound and an Au-containing precursor compound are sprayed from a mixed solution containing both precursor compounds onto the support body. In this case, the Pd-containing precursor compound is preferably $Pd(NH_3)_4(OH)_2$ and the Au-containing precursor compound is preferably $NaAuO_2$ or $KAuO_2$, more preferably $KAuO_2$.

After the optional step of drying the support body after step (b), it can optionally be subjected to a thermal treatment in a nonoxidizing atmosphere for reduction of the metal components of the precursor compound to the elemental metals, before step (c) is conducted. In this case, the support body used in step (c) already contains Pd and Au in elemental form. The metals here are either in monoatomic form or in the form of aggregates. However, they are preferably in the form of aggregates. These monoatomic atoms or aggregates are dispersed predominantly homogeneously within the shell of the eggshell catalyst.

The Pd-containing and Au-containing support body which is used in the process according the invention can, however, also be used directly after the drying operation, without reducing the metal components in the precursor compounds applied to the elemental metal. This embodiment is more preferred in accordance with the invention.

If the support body, after step (b), is subjected to a thermal treatment in a nonoxidizing atmosphere, this thermal treatment is preferably conducted within a temperature range from 80° C. to 500° C.

A nonoxidizing atmosphere is understood in the present invention to mean an atmosphere comprising no or virtually no oxygen or other oxidizing gases. The nonoxidizing atmosphere may be an atmosphere of inert gas or a reducing atmosphere or a mixture of the two gas variants.

In one variant of the process according to the invention, the reduction is conducted in an atmosphere of inert gas. In this case, the counterions of the metal ion in the metal-containing precursor compound have a reducing effect, or the metal complexes disproportionate under the selected process conditions to the zero oxidation state.

In a further variant of the process according to the invention, the thermal treatment can be conducted directly in a reducing atmosphere. In this case, the precursor compounds are decomposed at the same thermal treatment temperature and the metal component is reduced to the elemental metals. In other words, decomposition and reduction are performed simultaneously at the same temperature in the reducing atmosphere. In this case, the thermal treatment preferably takes place within a range from greater than or equal to 40° C. to 400° C., more preferably 50° C. to 300° C., even more preferably 60° C. to 250° C. and most preferably in the range from 70° C. to 180° C.

In yet a further variant of the process according to the invention, the thermal treatment is preferably conducted in such a way that, during the thermal treatment, there is a changeover from an atmosphere of inert gas to a reducing atmosphere. In this case, the precursor compounds are first decomposed at their decomposition temperature in an atmosphere of inert gas, and then, as a result of the changeover to a reducing atmosphere, the metal components are reduced to the elemental metals. The temperature during the decomposition under inert gas is preferably in the range from 200 to 500° C., more preferably 250 to 450° C. and most preferably above 300° C. The temperature during the subsequent reduction is then preferably in the range from greater than or equal to 40° C. to 400° C., more preferably 40° C. to 300° C., even more preferably 45° C. to 250° C. and most preferably in the range from 50° C. to 180° C.

All three process variants have the advantage that it is possible to dispense with a preliminary calcination or intermediate calcination in a further upstream or intermediate step in another plant. Therefore, the process according to the invention is preferably conducted in such a way as to be able to dispense with costly and inconvenient cooling to below the decomposition temperature and heating to above the decomposition temperature. Therefore, this process is energy- and cost-efficient. This was possible especially since the starting materials are compounds which do not have such high decomposition temperatures, for example chlorine compounds.

According to the invention, it is particularly preferable that the changeover from an atmosphere of inert gas to a reducing atmosphere is conducted in such a way that the temperature during the changeover does not fall below the temperature desired for the reduction.

Inert gases used are, for example, $N_2$, He, Ne, Ar or mixtures thereof. Particular preference is given to using $N_2$.

The reductive component in the reducing atmosphere should generally be selected depending on the nature of the metal component to be reduced, but is preferably selected from the group of gases or evaporable liquids consisting of ethylene, hydrogen, CO, $NH_3$, formaldehyde, methanol, formic acid and hydrocarbons, or is a mixture of two or more of the aforementioned gases/liquids. More preferably, the reducing atmosphere comprises hydrogen as reducing component. It is especially preferable when the reducing atmosphere is formed from forming gas, a mixture of $N_2$ and $H_2$. The hydrogen content here is within the range from 1% by volume to 15% by volume. The process according to the invention is conducted, for example, with hydrogen (4-5% by volume) in nitrogen as process gas at a temperature in the range from 80° C. to 500° C. over a period of, for example, 1 to 5 hours.

The changeover from inert gas to a reducing atmosphere mentioned in the second process alternative is preferably effected by feeding one of the reducing components mentioned into an atmosphere of inert gas. Preference is given here to feeding in hydrogen gas. The feeding of a reducing gas into the inert gas has the advantage that the temperature does not fall significantly, and does not fall to or below the lower limit of 80° C. desired for the reduction, and so no costly and energy-intensive reheating resulting from a corresponding total atmosphere exchange is needed.

In a particularly preferred embodiment, the support body comprising the precursor compounds, prior to the thermal treatment, is not exposed to a temperature of greater than or equal to 300° C. in an oxidizing atmosphere. In this way, it is ensured that the support body together with the precursor compounds applied thereto is subjected to the thermal treatment in the same way as the precursor compounds. In other words: it is possible to dispense with a costly preliminary calcination of the impregnated support body to the metal oxides. However, it is also possible in accordance with the invention that an intermediate calcination to oxides is conducted.

The impregnation with the Au-containing precursor compound in step (c) onto the support body is preferably effected in the process according to the invention in the same way as the impregnation of the support body with the Pd-containing and Au-containing precursor compounds in step (b). Especially preferably, the solution is carried out here onto the support body by means of a fluidized bed—as described above. More preferably, the IAC-5 pilot coater or the IAC-150 production coater from Innojet is used here too. Preference is given to using the same solvents in step (c) as in step (b). More particularly, deionized water is used here as solvent.

The solution comprising the Au-containing precursor compound from step (c) contains Au preferably within the range from 0.01 to 5% by weight, more preferably within the range from 0.05 to 2% by weight and most preferably 0.08 to 1% by weight, based on the atomic proportion by weight of the metal in the overall solution. If the metal contents are above the ranges specified in the solution, the result is eggshell catalysts having a lower selectivity. Metal contents below the ranges specified have an adverse effect on the activity of the catalysts obtained.

After the application (impregnation) of the solution in step (c), the support body is preferably dried in the same way as specified above in connection with the optional drying of the support body after step (b). The same details apply with regard to the temperature range and the process air.

After the solution comprising the Au-containing precursor compound has been applied to the support body in step (c), and the support body has been dried, the resulting support body is subjected to a thermal treatment in a nonoxidizing atmosphere for metal reduction. In the course of this, the metal components of the precursor compounds are reduced to the elemental metals.

If the Pd and Au applied in step (b) are still present in the form of the precursor compounds thereof, or are already present in the form of their oxides as a result of the optional intermediate calcination, the thermal treatment is conducted after step (c) in a nonoxidizing atmosphere, preferably in the manner described above. If the Pd and Au applied in step (b) are already in elemental form before step (c), prior to the thermal treatment after step (c), it is possible to dispense with either the optional calcination to give the metal oxides or the abovementioned decomposition of the precursor compound, and to conduct the thermal treatment in a nonoxidizing atmosphere within a temperature range from 60° C. to 200° C., preferably 70° C. to 160° C. It is also possible to subject the catalyst support body to a calcination in a nonoxidizing atmosphere prior to the thermal treatment. Preferably, however, the thermal treatment for reduction is conducted directly after the drying step.

The application of a solution comprising the Au-containing precursor compound to a catalyst support body in step (c), the latter already containing Pd and Au in one of the forms mentioned, is also referred to in accordance with the invention as post-gilding.

In step (c) of the process according to the invention, preference is given to applying a further amount of Au in the range from 0.01 to 1.2% by weight, more preferably 0.02 to 1.1% by weight, even more preferably 0.04 to 0.9% by weight, even more preferably 0.06 to 0.7% by weight, even more preferably 0.08 to 0.4% by weight and most preferably 0.1 to 0.2% by weight, based on the total weight of the dry eggshell catalyst.

The eggshell catalyst produced by the process according to the invention thus preferably contains a total Au content in the range from 0.1 to 1.2% by weight, more preferably 0.2 to 1.0% by weight, even more preferably 0.3 to 0.8% by weight and most preferably in the range from 0.4 to 0.7% by weight, based on the total weight of the eggshell catalyst.

In the last step, the KOAc (potassium acetate) promoter is applied to the post-gilded support by impregnating the catalyst precursor with an aqueous KOAc (potassium acetate) solution (preferably aqueous solution) by the pore-filling (incipient wetness) method at room temperature, and typically leaving it to stand for about one hour before commencement of drying. The potassium loading is preferably in the range from 2 to 3.5% by weight, more preferably 2.2 to 3.0% by weight and most preferably 2.5 to 2.7% by weight, based on the total weight of the dry catalyst. The application of the KOAc (potassium acetate) solution may be followed by a final drying operation in the range of 70-120° C., more preferably 80-110° C. and most preferably 90-100° C. in air, lean air or inert gas.

The present invention further provides, in addition, an eggshell catalyst obtainable by the process according to the invention. The inventive eggshell catalyst differs from conventional eggshell catalysts for the synthesis of VAM in that it has a significantly higher selectivity and activity in the synthesis of VAM. The structural differences which clearly exist on the basis of the better selectivity and activity of the inventive eggshell catalyst compared to conventional catalysts cannot be expressed in physical parameters at the time of filing. Therefore, the inventive eggshell catalyst can be distinguished from conventional catalysts only via the method of preparation thereof and the elevated selectivity and activity found.

A further embodiment relates to the use of an eggshell catalyst produced by a process according to the invention for oxyacetylation of olefins, especially for preparation of allyl acetate or vinyl acetate (VAM). In other words, the present invention also relates to a process for oxyacetylation of olefins, in which acetic acid, an olefin and oxygen or oxygen-containing gases are passed over the inventive catalyst. Olefin here is preferably ethylene or propylene. The process is generally effected by passing acetic acid, an olefin and oxygen or oxygen-containing gases over the inventive catalyst at temperatures of 100-200° C., preferably 120-200° C., and at pressures of 1-25 bar, preferably 1-20 bar, and unconverted reactants can be circulated. Appropriately, the oxygen concentration is kept below 10% by volume. Under some circumstances, however, dilution with inert gases such as nitrogen or carbon dioxide is also advantageous. Particularly carbon dioxide is suitable for dilution, since it is formed in small amounts in the course of the VAM synthesis and accumulates in the cycle gas. The vinyl acetate/allyl acetate formed is isolated with the aid of suitable methods described, for example, in U.S. Pat. No. 5,066,365 A.

The invention is elucidated in detail hereinafter by a FIGURE and by working examples, but these should not be understood in a restrictive manner.

FIGURE

FIG. 1 shows the VAM selectivity calculated from the measurement of VAM and $CO_2$ peaks as a function of the $O_2$ conversion using six different eggshell catalysts in the catalytic synthesis of VAM.

EXAMPLES

The percentages based on the solutions comprising the precursor compounds are atomic percentages by weight of the respective metal based on the total weight of the solution.

Comparative Example 1: Production of Catalyst A1

To produce catalyst A1, 2200 g of KA-Zr14 supports (5 mm spheres, $ZrO_2$ content 14%, precalcined at 750° C. for 4 h in air) were coated in the Innojet IAC-5 pilot coater at 70° C. with a mixed solution composed of 1027.38 g of 2.8% $Pd(NH_3)_4(OH)_2$ solution (spray rate 30%, i.e. a mass flow rate of 18 g/min) and 230.06 g of 5.21% $KAuO_2$ solution and 100 mL of water (spray rate 30%, i.e. mass flow rate 18 g/min), and then dried in situ in the pilot caster at 87° C. for 40 min. Then reduction was effected in the gas phase with 5% $H_2/N_2$ at 160° C. for 4 h. Finally, the catalyst precursor was impregnated with an aqueous KOAc (potassium acetate) solution (1358 mL of a 1,087 molar=10.565% by weight aqueous KOAc (potassium acetate) solution; prepared by diluting 738.11 of a 2 molar KOAc (potassium acetate) stock solution with 619.95 mL of water) by the pore-filling (incipient wetness) method at room temperature and left to stand for 1 h and then dried in a fluidized bed drier at 90° C. for 45 min. In this way, catalyst A1 was obtained with an amount of Pd of 1.2% by weight and an amount of Au of 0.5% by weight, based on the total weight of the catalyst. The elemental analysis of all the examples was conducted with an ICP Spectro Arcos after grinding of the catalyst and digestion.

Comparative Example 2: Production of Catalyst A2

Catalyst A2 was produced in the same way as catalyst A1, but with the following differences:

For the application of the solution, the Innojet IAC-025 laboratory coater was used. 100 g of KA-Zr14 support were used, and the solutions applied were the following:
46.65 g of 2.8% $Pd(NH_3)_4(OH)_2$ solution
8.36 g of 5.2% $KAuO_2$ solution Reduction was effected at 150° C. for 4 h. In this way, catalyst A2 was obtained with an amount of Pd of 1.2% by weight and an amount of Au of 0.4% by weight, based on the total weight of the catalyst.

Comparative Example 3: Production of Catalysts A3 and A4

In the same way as catalyst A1, catalysts A3 and A4 were produced, with the difference that the amount of Au was varied accordingly so as to obtain catalysts having the following amounts of Au and Pd:
A3: Pd: 1.2% by weight Au: 0.6% by weight
A4: Pd: 1.2% by weight Au: 0.7% by weight The percentages by weight are each based on the proportion of the metals, based on the total weight of the catalyst.

Comparative Example 4: Production of Catalyst B

Catalyst B was produced like catalyst A2, but with the following differences:
31.84 g of 3.415% Pd solution
10.43 g of 5.21% Au solution In the course of coating, a temperature ramp in the coating temperature was employed: the coating temperature was increased during the coating operation from 55° C. to 70° C.

In this way, a catalyst having a Pd content of 1.0% by weight and an Au content of 0.5% by weight was obtained.

Comparative Example 5: Production of Catalyst C

Catalyst C was produced like catalyst B, with the difference that, in the coating process, the temperature during the coating operation was lowered from 70° C. to 55° C.

In this way, a catalyst having a Pd content of 1.0% by weight and an Au content of 0.5% by weight was likewise obtained.

Example 1: Production of Inventive Catalyst D

To produce catalyst D, 2200 g of KA-Zr14 supports (5 mm spheres, $ZrO_2$ content 14%, precalcined at 750° C. for 4 h in air) were coated in the Innojet IAC-5 pilot coater at 70° C. with a mixed solution composed of 1027.38 g of 2.8% $Pd(NH_3)_4(OH)_2$ solution and 230.06 g of 5.21% $KAuO_2$ solution and 100 mL of water (spray rate 30%, i.e. with a mass flow rate of 18 g/min), and then dried in situ in the pilot coater at 87° C. for 40 min. 100 g of the catalyst support obtained were then initially charged and coated with 2.06 g of 5.21% $KAuO_2$ solution in 100 mL of water at 70° C. in the IAC-025 laboratory coater (spray rate 30%, i.e. a mass flow rate of 3.5 to 5 g/min) and then dried in a fluidized bed drier at 90° C. for 45 min and then reduced in the gas phase with 5% $H_2/N_2$ at 150° C./4 h and subsequently impregnated with a KOAc solution as in comparative example 1 and finally dried in a fluidized bed at 90° C./45 min. In this way, a post-gilded catalyst was obtained with a Pd content of 1.2% by weight and an Au content of 0.6% by weight.

Example 2: Production of Inventive Catalyst E

Catalyst E was produced like catalyst D, with the sole difference that 4.12 g of a 5.21% $KAuO_2$ solution were used. In this way, a post-gilded catalyst having a Pd content of 1.2% by weight and an Au content of 0.7% by weight was obtained.

Example 3: Test Results of Catalysts A1 to A4 and B to E in Terms of Selectivity Thereof in the Synthesis of Vinyl Acetate Monomer For this purpose, acetic acid, ethylene and oxygen were passed over each of catalysts A1 to A4 and B to E at a temperature of 140° C./12 h→143° C./12 h→146° C./12 h (these are the respective reaction temperatures set in sequence in the automated running of the screening protocol, i.e. measurement is effected at reactor temperature 140° C. for 12 h, then at 143° C. for 12 h, and then at 146° C. for 12 h) and a pressure of 6.5 bar. The concentrations of the components used were: 39% ethylene, 6% $O_2$, 0.6% $CO_2$, 9% methane, 12.5% acetic acid, remainder $N_2$.

In a preliminary test, the optimal Au content was first determined at a content of 1.2% by weight of Pd. For this purpose, selectivity was determined as a function of the $O_2$ conversion of catalysts A1 to A4. It was found that a catalyst having an Au content of 0.5% by weight of Au has the best selectivity and activity, i.e. catalyst A1 has a better performance than catalysts A2, A3 and A4 having higher and lower Au contents.

Subsequently, the inventive catalysts D and E were tested in comparison with the comparative catalysts A1, A2, B and C.

FIG. 1 shows the VAM selectivity of catalysts A1, A2 and C to E as a function of the $O_2$ conversion. The values are additionally listed in tabular form in tables 1 and 2:

TABLE 1

| Catalyst A2 | | Catalyst A1 | | Catalyst D | |
|---|---|---|---|---|---|
| VAM selectivity calculated from VAM and CO2 peaks [%] | O2 conversion [%] | VAM selectivity calculated from VAM and CO2 peaks [%] | O2 conversion [%] | VAM selectivity calculated from VAM and CO2 peaks [%] | O2 conversion [%] |
| 94.4 | 42.9 | 94.9 | 38 | 94.6 | 47.2 |
| 94.4 | 43.4 | 94.8 | 37.8 | 94.7 | 47.5 |
| 94.5 | 43.5 | 95 | 37.7 | 94.7 | 47.7 |
| 94.5 | 43.9 | 95 | 37.6 | 94.7 | 47.2 |
| 94.1 | 48.5 | 94.7 | 41.3 | 94.3 | 51.9 |
| 94 | 48.8 | 94.7 | 41.1 | 94.4 | 51.8 |
| 94.1 | 48.4 | 94.7 | 41.3 | 94.4 | 52 |
| 94.2 | 48.6 | 94.6 | 40.8 | 94.4 | 51.6 |
| 94.3 | 48.7 | 94.7 | 40.9 | 94.4 | 51 |
| 93.8 | 55 | 94.4 | 45.4 | 94 | 56.9 |
| 93.8 | 54.5 | 94.6 | 45.4 | 94 | 56.5 |
| 93.8 | 54.2 | 94.4 | 45.2 | 94.1 | 56.1 |
| 93.8 | 54.4 | 94.4 | 45 | 94.1 | 56.1 |
| 93.8 | 54.2 | 94.4 | 44.5 | 94.1 | 55.6 |
| 93.2 | 59.4 | 94.1 | 49.2 | 93.5 | 61.3 |
| 93.4 | 59.5 | 94.1 | 48.4 | 93.6 | 60.4 |
| 93.5 | 58.9 | 94.1 | 48.6 | 93.7 | 60.3 |
| 93.4 | 59 | 94.1 | 48.2 | 93.6 | 59.9 |
| 93.5 | 58.5 | 94.1 | 48.3 | 93.7 | 59.8 |
| 94.6 | 48.3 | 95 | 40.2 | 94.9 | 49.9 |
| 94.6 | 48 | 95 | 39.6 | 94.9 | 49.6 |
| 94.7 | 47.9 | 95 | 39.6 | 94.8 | 49.5 |
| 94.7 | 47.8 | 95 | 39.5 | | |

TABLE 2

| Catalyst E | | Catalyst B | | Catalyst C | |
|---|---|---|---|---|---|
| VAM selectivity calculated from VAM and CO2 peaks [%] | O2 conversion [%] | VAM selectivity calculated from VAM and CO2 peaks [%] | O2 conversion [%] | VAM selectivity calculated from VAM and CO2 peaks [%] | O2 conversion [%] |
| 94.5 | 45.3 | 94.7 | 34.7 | 94.7 | 38.7 |
| 94.6 | 45.4 | 94.7 | 35.4 | 94.8 | 38.7 |
| 94.7 | 45.5 | 94.8 | 34.8 | 94.9 | 38.8 |
| 94.5 | 46.6 | 94.5 | 38.2 | 94.5 | 42.9 |
| 94.2 | 49.6 | 94.4 | 38.1 | 94.5 | 42.8 |
| 94.4 | 49.4 | 94.4 | 38.6 | 94.6 | 43 |
| 94.3 | 49.3 | 94.5 | 38.4 | 94.6 | 42.8 |
| 94.4 | 49.2 | 94.7 | 38.8 | 94.7 | 43.2 |
| 94.4 | 49.1 | 94.3 | 41.5 | 94.3 | 47.6 |
| 93.8 | 53.8 | 94.2 | 42.6 | 94.3 | 47.9 |
| 94 | 53.8 | 94.4 | 43.2 | 94.3 | 47.9 |
| 94 | 53.3 | 94.3 | 43.1 | 94.3 | 47.2 |
| 94.1 | 53.1 | 94.3 | 42.7 | 94.4 | 47.3 |
| 94 | 53.2 | 94.3 | 42.7 | 94.3 | 48.3 |
| 93.5 | 57.7 | 94 | 47.0 | 94 | 52 |
| 93.5 | 57.3 | 94.1 | 46.7 | 94 | 51.5 |
| 93.5 | 57 | 94.1 | 46.2 | 94.2 | 51.7 |
| 93.7 | 56.6 | 94 | 46.5 | 94 | 51.4 |
| 93.6 | 56.6 | 94.1 | 46.1 | 94 | 51.4 |
| 94.7 | 47.7 | 94.9 | 38.2 | 95 | 42.6 |
| 94.8 | 47.3 | 95 | 38.2 | 95 | 42.6 |
| 94.8 | 47.2 | 95 | 39 | 95 | 42.7 |

As is apparent from the comparison of the values from tables 1 and 2 and FIG. 1, the catalysts produced in accordance with the invention have a much higher selectivity, coupled with equal or higher activity ($O_2$ conversion), than the comparative catalysts A1, A2, B and C.

The invention claimed is:

1. A process for producing an eggshell catalyst, comprising the steps of:
    (a) subjecting a bed of a catalyst support body to a circulating motion;
    (b) contacting an atomized aqueous solution comprising a Pd-containing precursor compound and an Au-containing precursor compound with the bed of the catalyst support body subjected to the circulating motion by spraying;
    (c) contacting an atomized aqueous solution comprising an Au-containing precursor compound with the catalyst support body obtained after step (b); and
    (d) metal reduction by subjecting the catalyst support body obtained in step (c) to a thermal treatment in a nonoxidizing atmosphere and
    wherein the Au-containing precursor compounds in steps (b) and (c) are, independently, compounds selected from the group consisting of hydroxidic metalate compounds.

2. The process as claimed in claim 1, wherein the contacting in step (c) includes spraying the solution onto a bed of the catalyst support body subjected to a circulating motion.

3. The process as claimed in claim 2, wherein the circulating motions are conducted with the aid of a process gas.

4. The process as claimed in claim 2, wherein the circulating motions take place in a moving bed or fluidized bed.

5. The process as claimed in claim 1 wherein the thermal treatment is conducted within a range from 40° C. to 500° C.

6. The process as claimed in claim 1, wherein the ratio of the weight of the solution sprayed on in step (b) or (c) to the weight of the bed of the catalyst support body is within the range from 0.005 to 0.1.

7. The process as claimed in claim 1, wherein the catalyst support body after step (b) has a Pd content in the range from 0.5 to 2.5% by weight, based on the total weight of the catalyst support body.

8. The process as claimed in claim 1, wherein the catalyst support body after step (b) has an Au content in the range from 0.2 to 1.0% by weight, based on the total weight of the catalyst support body.

9. The process as claimed in claim 1, wherein the eggshell catalyst has an Au content in the range from 0.25 to 1.2% by weight, based on the total weight of the eggshell catalyst.

10. The process as claimed in claim 1, wherein the Pd-containing precursor compound is a compound selected from the group consisting of a nitrate compound, nitrite compound, acetate compound, tetraammine compound, diammine compound, hydrogencarbonate compound, hydroxidic metalate compounds and mixtures thereof.

11. The process as claimed in claim 1, wherein the nonoxidizing atmosphere comprises a reducing agent.

12. The process as claimed in claim 11, wherein the reducing agent is hydrogen.

13. The process as claimed in claim 1, wherein the support body is impregnated with KOAc (potassium acetate) after the thermal treatment.

14. A process for producing an eggshell catalyst, comprising the steps of:
    (a) subjecting a bed of a catalyst support body to a circulating motion;
    (b) contacting an atomized aqueous solution comprising a Pd-containing precursor compound and an Au-containing precursor compound with the bed of the catalyst support body subjected to the circulating motion by spraying;
    (c) contacting an atomized aqueous solution comprising an Au-containing precursor compound with the catalyst support body obtained after step (b); and
    (d) metal reduction by subjecting the catalyst support body obtained in step (c) to a thermal treatment in a nonoxidizing atmosphere and
    wherein the Au-containing precursor compounds in steps (b) and (c) are, independently,
    $NaAuO_2$, $KAuO_2$, $LiAuO_2$ or $RbAuO_2$.

* * * * *